United States Patent [19]

Lary

[11] Patent Number: 5,156,150
[45] Date of Patent: Oct. 20, 1992

[54] METHOD OF USE OF SPECIMEN APPARATUS

[76] Inventor: Banning G. Lary, Suite 411, 6280 Sunset Dr., Miami, Fla. 33143

[21] Appl. No.: 619,341

[22] Filed: Jan. 28, 1991

Related U.S. Application Data

[62] Division of Ser. No. 536,860, Jun. 8, 1990, Pat. No. 4,993,056.

[51] Int. Cl.⁵ .............................................. A61B 5/00
[52] U.S. Cl. .................................... 128/630; 128/898
[58] Field of Search ................... 128/898, 630, 653 R

[56] References Cited

U.S. PATENT DOCUMENTS 4,821,727  4/1989  Levene et al. .................. 128/653 R
5,050,725  9/1991  Levy ................................... 128/630

Primary Examiner—William E. Kamm
Assistant Examiner—Scott R. Akers
Attorney, Agent, or Firm—Robert J. Van der Wall

[57] ABSTRACT

The invention describes a method of use of a specimen support comprising a specimen board with an absorbent square attached thereto, radio-opaque indicia attached to the specimen board, a compression sheet hingedly attached to the specimen board and means for attaching the board and sheet together at a location remote from the hinge. The method includes use of the apparatus for diagnostic studies including radiologically localizing internal structure of a specimen carried by the board and for pathological study of the specimen and reporting of the results of such diagnostic studies.

8 Claims, 1 Drawing Sheet

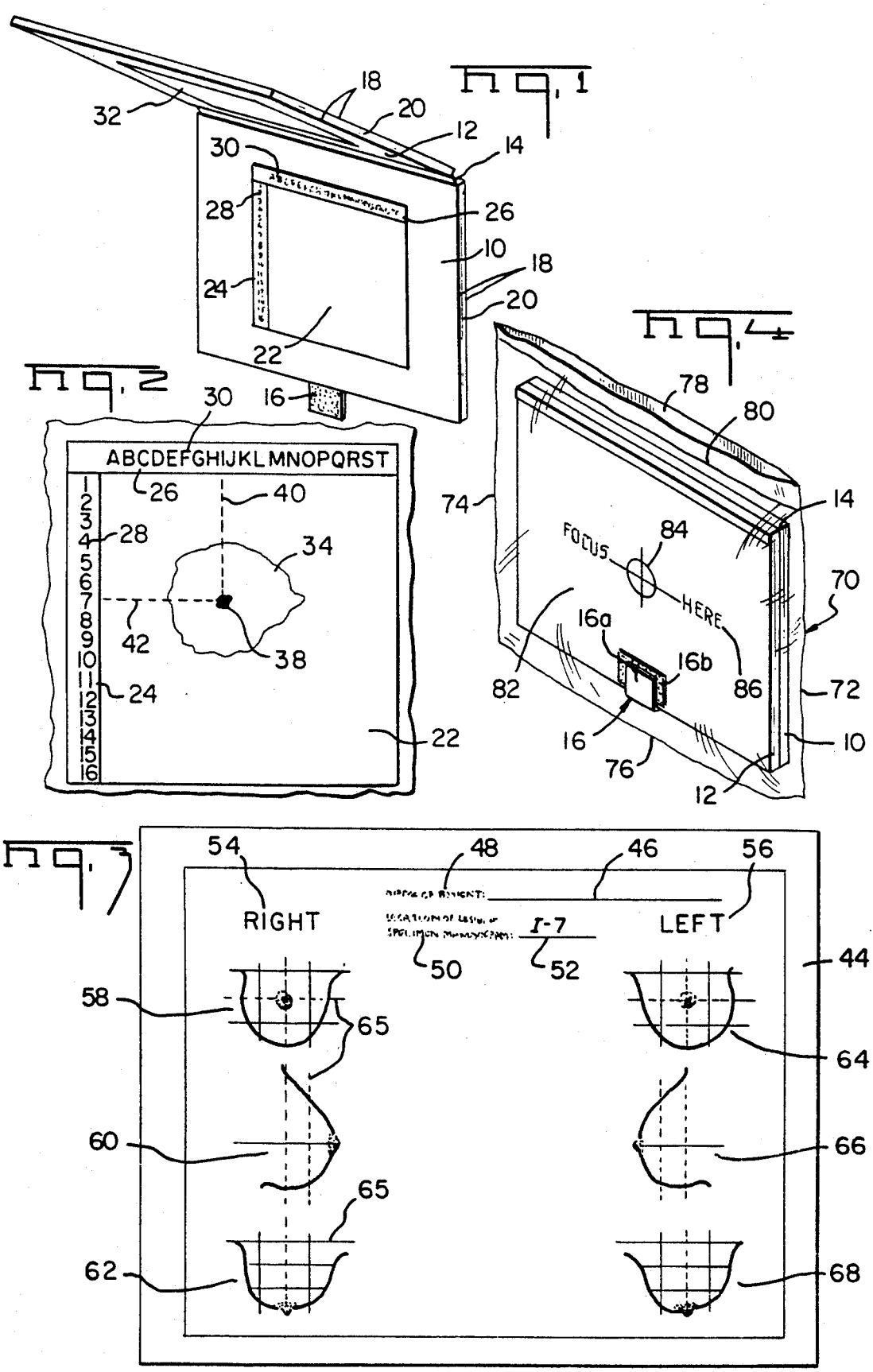

METHOD OF USE OF SPECIMEN APPARATUS

CROSS-REFERENCE TO RELATED APPLICATION

This application is a division of application Ser. No. 07/534,860 filed Jun. 8, 1990, now U.S. Pat. No. 4,993,056.

FIELD OF THE INVENTION

The present invention relates to the medical field of pre-operative localization and biopsy of nonpalpable breast lesions. More particularly, the invention concerns a method of use of an apparatus to which an excised specimen is attached in a manner which allows the surgeon to establish that the lesion has been removed and which facilitates finding the lesion within the specimen by the pathologist.

BACKGROUND OF THE INVENTION

Detection of small, nonpalpable breast lesions has been greatly facilitated in recent years by the use of x-ray, mammography and/or sonography procedures. However, identification of a suspicious lesion does not establish its exact location within the breast. Heretofore, needle location of suspicious lesions using radiology has been a common approach. Some special variations have also been employed including a modified needle/hook wire technique.

Surgical excision has, in the past, resulted in several interrelated difficulties that contribute to inefficiency and inaccuracy. These difficulties include the fact that location of the lesion within the specimen is complicated by movement of the specimen on the x-ray film during transportation to pathology and during the pathological analysis. Further, this technique requires an extended period of anesthesia for the patient and is subject to inaccuracies and inconsistencies in the interpretation and communication to the surgeon of the pathologist's findings.

The present invention is the method of using an apparatus to secure the specimen during the transportation and pathological analysis in relation to a precise location defined by radio-opaque coordinates superimposed on the x-ray. In addition, the inclusion of a fixed orientation and radio-opaque coordinates for the excised specimen on the x-ray is extremely beneficial to the pathologist in localization of the suspicious lesion within the specimen to avoid a misdiagnosis.

The difficulties addressed by the present invention have also been recognized by the prior art as disclosed by a pre-examination search. The most relevant reference recognizing these concerns, and disclosed by the search, is Gabrielle et al., U.S. Pat. No. 4,691,333, which discloses a breast compression plate apparatus in combination with a mammographic film cartridge and attaching means therebetween which compression plate has a plurality of perforations disposed in a matrix for needle localization of breast lesions. However, this disclosure suffers from the difficulty that it can only be utilized in a single plane at one time, although separate use in two perpendicular planes is illustrated. Movement of the breast is restricted during the localization procedure in a given plane, but is not achievable when the disclosed apparatus is repositioned to a perpendicular plane. Contrariwise, the present invention contemplates three dimensional localization because of the use of a matrix of lines on a three dimensional diagrammatic representation of each breast rather than localization using a compression plate or similar physical apparatus that must be moved for two dimensional use, and must be removed during the surgical procedure.

Other references disclose the use of radio-opaque indicia in combination with x-rays. Cherry, U.S. Pat. No. 3,547,121, describes a radio-opaque grid for use with x-ray positioning of a needle for a fetal transfusion. The grid is attached to the pregnant women's abdomen and is used to identify in combination with x-ray the location of the fetus in the peritoneal cavity so that placement of the needle for injection of the fetus can be performed accurately. In this instance, the grid is left in place on the patient during the procedure to coordinate with the x-ray result after the same is developed.

A further and similar reference, is Vitalini, U.S. Pat. No. 4,181,859, which discloses a grid image printed in radio-opaque ink and adhesively attached to x-ray film to facilitate measurement on the exposed x-ray. It is adapted for use with flexible radiographic films that are commonly used in dentistry, and achieves a two-dimensional result even though the x-ray film undergoes the substantial deformations that are usual in dental radiography.

A further reference of lesser relevance is Bliss, U.S. Pat. No. 2,399,424, which discloses scales or indicia on the edge of an x-ray film to measure foot length and width and shoe size in connection with the fitting of shoes.

As more fully described hereinafter, the apparatus used in present invention also includes an absorbent square to which the specimen naturally adheres, a compression sheet placed over the specimen to obtain compression radiography, a target for positioning the specimen in the x-ray machine, and a sealable enclosure for transporting the specimen. The pre-examination search also revealed two references of very modest relevance to these latter aspects of the invention. The first of these references is Ammerman, U.S. Pat. No. 4,723,974, which teaches a transporting container for an amputated extremity. The reference discloses a multi-wall, flexible container intended to provide a cooling compartment to achieve a decreased temperature environment for the amputated extremity disposed within the inner compartment. The other reference is Winchell, U.S. Pat. No. 4,474,016 which teaches a sterile cooling system for organs during transplant surgery. The latter reference also discloses techniques for temperature reduction using a multi-layer structure.

SUMMARY OF THE INVENTION

Bearing in mind the foregoing is a principal object of the present invention to provide method of using a specialized apparatus to simplify the pre-operative localization and biopsy of nonpalpable breast lesions.

A related object of the invention is to provide a method that simplifies the pre-operative localization and biopsy of nonpalpable breast lesions.

A further object of the invention is to provide a method for said localization that minimizes inaccuracies and inconsistencies present in the prior art techniques including especially simple needle localization.

An additional object of the invention is to avoid shifting of a specimen on an x-ray film during transportation from the operative site to the pathology laboratory and when the specimen is being cut by the pathologist.

Another object of the invention is to improve the precision in defining the exact location of the lesion in a specimen, using specimen radiography, in combination with the image of radio-opaque indicia superimposed on the x-ray film.

One more object of the invention is to provide for use with the inventive method a simplified, inexpensive, disposable apparatus in the form of a specimen board in combination with an absorbent square to which the specimen naturally adheres to fix the specimen during transportation to specimen radiography and thence transportation to and examination in the pathology laboratory.

A further object of the invention is to combine said procedure with use of a resealable enclosure for ease of transportation of the specimen without contamination thereof.

A further object of the invention is the combination of the use of the absorbent square with radio-opaque indicia to greatly improve localization accuracy and reporting by specimen radiography.

A related object of the invention is to combine the foregoing features and objectives with use of a compression sheet preferably fabricated from the same material as the specimen board and which is hingedly attached thereto. It is preferably held in position using hook and loop fastening means.

Another object of the invention is to combine the foregoing features with use of a diagram in three views of the breast and a matrix of lines so the medical team can mark in three dimensions the location of the specimen and suspicious lesions.

A further object of the invention is to establish a method for use of each of the foregoing features and objectives in an efficient and reproducible manner.

Other objects and advantages of the present invention will be apparent to those skilled in the art upon review of the following descriptions and the drawings.

In accordance with one aspect of the invention, there is provided method for use of a specimen board comprised of a foam core sheet of a sandwich construction having adhesively attached to both sides of the core of an expanded polymer smooth, preferably white, paper. The specimen board is preferably eight by ten inches in lateral dimensions and one-quarter of an inch thick. On one side of the foam core sheet is attached at right angles to each other two strips of radio-opaque material, preferably copper sheet, which has been punched with a series of indicia one strip preferably including a series of numbers and the other strip a series of letters. These indicia serve to border two of the four edges of a square absorbent material, such as a blotter, which is adhesively attached to the specimen board adjacent to these two strips.

At the upper edge of the specimen board is attached a flexible strip. A second foam core sheet is also attached to the flexible strip rendering said flexible strip as a hinge. Attached to the second sheet, which will be called a compression sheet, is a specimen cover square which is release coated having dimensions and a location such that the specimen cover square is superimposed directly above the absorbent material square on the specimen board with its adjacent strips of radio-opaque material. This is accomplished utilizing the hinge formed by the flexible strip between the two foam core sheets. When the compression sheet is folded over the specimen board, it can be attached in position using fastening means, preferably a hook and loop fastener of the type sold under the trademark "velcro" (registered trademark of Velcro Corp.). The specimen naturally adheres to the absorbent square, but will not adhere to specimen cover square because of its release coating. The coating is preferably teflon (registered trademark of duPont) or a silicone material.

Another aspect of the invention includes use of an enclosure in which the fastened specimen board and compression sheet can be inserted with the specimen therebetween. This enclosure is preferably a flat plastic bag having lateral dimensions slightly larger than those described above for the two foam core sheets forming the specimen board and compression sheet. It is typically fabricated from polyethylene or similar plastic material, is preferably transparent, and preferably has a resealable closure means at the open end.

The combination of the specimen board and compression sheet hingedly connected together are disposed within the enclosure when delivered to the surgeon at the operative site. Also contained in the enclosure is a sheet of paper which has been printed with three views each of a left and right breast, labeled accordingly, and with a matrix of lines to be used for identifying the location of the specimen within the breast, thereby localizing any following medical procedure concerning the breast. This paper also contains a blank for writing in the name of the patient. Printed on one side thereof are diagrammatic and written instructions of a suggested technique for use, which define, in outline form, at least a portion of the inventive method.

Including in this method are various steps including: Using mammography, suspicious lesions are identified and their position established temporarily utilizing a localizing needle. Then, on the diagram of the breasts, the positions are identified using the matrix of lines. A specimen is then removed, placed on the specimen board, on the absorbent square, to which it naturally adheres, the compression sheet is hingedly folded over the specimen, the same being secured with the hook and loop fastener attached to the lower edges of the specimen board and compression sheet and the same is then inserted into the enclosure. It is transported to radiology to perform specimen radiography. The radiologist then marks the location of the lesion and writes the location in the blank provided on the sheet having the diagrams of the breast and then sends the specimen board to pathology.

In the pathological laboratory, the pathologist uses the information provided by specimen radiology to find the lesion in the specimen, cut the specimen on the specimen board at the location indicated, and after locating the lesion can perform the customary pathological studies including freezing for a receptor studies, freezing for an immediate section, and fixing for a permanent section. The results of the pathological procedure can be transmitted quickly to the surgeon at the operative site.

The invention will be better understood upon reference to the following detailed description and the drawings in which:

BRIEF DESCRIPTION OF THE DRAWINGS

FIG. 1 is a perspective view of the hinged combination of the specimen board and compression sheet in partially open position.

FIG. 2 is an enlarged broken plan view of the two strips of radio-opaque material showing the indicia thereon bordering two edges of the absorbent square.

FIG. 3 shows the diagrams of the breasts with matrix of lines for identification of the location of the specimen.

FIG. 4 shows the enclosure, in which has been placed the closed hinged combination of FIG. 1.

DETAILED DESCRIPTION OF PREFERRED EMBODIMENT

FIG. 1 illustrates in perspective view a specimen board 10 hingedly connected to a compression sheet 12. They are hingedly connected using a flexible strip 14 such that compression sheet 12 can be folded directly on top of specimen board 10 and attached thereto using a hook and loop fastener 16, a portion of which is attached to each. Specimen board 10 and compression sheet 12 are foam core sheets of sandwich construction having outer surfaces of smooth paper 18 and a foam core 20.

Centered on specimen board 10 and adhesively attached thereto is absorbent square 22 and being bordered on two of its edges strips of radio-opaque material 24 and 26. Strips 24 and 26 are punched with a series of indicia 28 and 30. Preferably, indicia 28 are a series of numbers such as from 1 through 16 and indicia 30 are letters such as A through T. Also seen on compression sheet 12 is adhesively attached release coated specimen cover square 32 which is configured and located to fold directly atop absorbent square 22.

Turning to FIG. 2, there is an enlarged broken view of absorbent square 22 bordered by radio-opaque strips 24 and 26. In this enlarged view the series of numbers 28 which are punched out of radio-opaque strip 24 can be read. Similarly, a series of letters 30 can be readily punched out of radio-opaque strip 26. Also seen in FIG. 2 is a specimen 34 which adheres to absorbent square 22 by reason of the latter's absorbency. Also seen therein is a lesion 38 contained within specimen 34. The position of the lesion 38 is established by reference to the radio-opaque indicia 28 and 30 such as shown with lines 40 and 42. In the illustrated example, the location of the lesion 38 is shown to be at I-7, but its location cannot be seen in actual practice with the naked eye. This location is established utilizing specimen radiology by the radiologist following removal of the specimen from the patient and transporting the same to the radiology department. Transportation is accomplished by the enclosure or flat plastic bag of FIG. 4 more fully described hereinafter.

Turning now to FIG. 3, there is a diagrammatic representation on a sheet of paper 44 that is furnished with the specimen board 10. Paper 44 has printed thereon a blank 46 for writing in the patient's name as indicated by description 48. Also contained on sheet 44 is description 50 and a blank 52 for the specimen radiologist to write in the location of the lesion within the specimen. In FIG. 3 the specimen radiologist is shown to have written in I-7 which is the location of the lesion within the specimen in FIG. 2. Also on sheet 44 are labels 54 and 56 indicating the right and left breasts. For each breast there is a front, lateral, and top view. For the right breast these are indicated as front view 58, lateral view 60 and top view 62. Each will be seen to have a matrix of lines 65 for identification of the location of the specimen by the surgeon. Similarly for the diagrams concerning the left breast 56, there are front view 64, side view 66 and top view 68. On the reverse side of sheet 44 (not shown) can be printed instructions concerning the inventive method as above described. Also included is a small diagram similar to FIG. 2 illustrating use by the specimen radiologist of the radio-opaque indicia to locate the lesion within the specimen for the benefit of the pathologist.

Turning to FIG. 4, there is illustrated an enclosure 70, preferably comprised of a flat polyethylene bag. It is sealed at its sides 72 and 74 and bottom 76, but is open at its top 78 as illustrated. The opening at the top 78, is preferably formed with a resealable closure means 80, such that the closed specimen board and compression sheet combination 82 containing a specimen may be inserted therein as shown and resealable closure means 80 can then completely enclose the specimen board 10 and compression sheet 12 with specimen 38 therein for transportation.

Also seen in FIG. 4 is a focusing target 84 which is printed on the back of compression sheet 12 to coincide with the center of the absorbent square 22 seen in FIGS. 1 and 2. It is preferably accompanied by written instructions "Focus Here" or the like, directed to the radiologist. Also seen are both portions of hook and loop fastener 16, comprised of 16a fixedly attached to specimen board 10, and 16b fixedly attached to compression sheet 12, with 16a and 16b being removably attached to each other to hold, in combination with flexible strip 14, specimen board 10 and compression sheet 12 tightly together for placement in enclosure 70 as shown.

In practice, the apparatus of the invention is utilized with the following inventive method. The specimen board 10 and compression sheet 12 combination is furnished to the surgeon at the operative site in the resealable enclosure 70 along with instructions and the diagrams of FIG. 3 as above-described.

The surgeon and radiologist utilize needle localization and radiography to temporarily establish the location of the suspicious lesion. The location is marked by the surgeon or one of his assistants on the diagrams of sheet 44. The specimen 34 is then removed from the breast and is placed on absorbent square 22 to which it adheres. Then, compression sheet 12 is folded over specimen 34 and firmly but removably attached using hook and loop fastener 16. The closed combination of the specimen board and compression sheet is then inserted into enclosure 70 which is sealed with resealable closure means 80. The same is then transported from the operating room to specimen radiology where the radiologist takes an x-ray. A focusing target 84 and instructions 86 assist the radiologist. The x-ray shows the location of lesion 38 within specimen 34, which is I-7 in the present example. The specimen radiologist then writes the location I-7 of the lesion on sheet 44 which is then placed back into enclosure 70 and resealed using resealable closure means 80. The enclosure 70 containing specimen 36 is then taken to the pathology laboratory. Using the information furnished from the specimen radiologist, the pathologist can then cut the specimen at the precise location defined by the specimen radiologist to perform the pathological study required. The results of this study and the exact location of the lesion can then be reported back to the surgeon by pathology.

Having described the presently preferred embodiments of the invention, it should be understood that various changes in construction and arrangement will be apparent to those skilled in the art and fully contemplated herein without departing from the true spirit of invention. Accordingly, there is covered all alternatives, modifications and equivalents as may be included within the spirit and scope of the invention as defined in the appended claims.

I claim:

1. A method of using a specimen apparatus comprising:

excising a specimen;

placing the specimen upon an absorbent square on a specimen board;

closing a compression sheet hingedly connected to the specimen board directly over the specimen;

removably attaching the specimen board and compression sheet together at a point distal from their hinge connection to enclose the specimen;

transporting the enclosed specimen to another location;

performing specimen radiology;

identifying, using said radiology, a precise location within a specimen of a suspected lesion;

noting coordinates of said lesion in relation to a radiographic image of radio-opaque indicia disposed in proximity to the specimen and lesion radiographic image;

performing a pathological procedure at a location in the specimen indicated by the coordinates of the lesion image; and reporting the result of said diagnostic study.

2. The method of claim 1 which further comprises placing the enclosed specimen in a resealable enclosure before transporting it.

3. The method of claim 1 which further comprises noting a particular location within a portion of a patient's anatomy of the specimen prior to excising it with respect to three views of said anatomy, each at right angles to each other in a diagrammatic representation, using a matrix of lines superimposed on the diagrammatic representation.

4. The method of claim 1 in which the radio-opaque indicia are letters and numbers punched out of copper strips attached to two adjoining edges of the absorbent square.

5. The method of claim 1 in which noting coordinates of the lesion comprises enscribing the coordinates on a writing surface that accompanies the specimen during the diagnostic study.

6. The method of claim 1 which further comprises using, during specimen radiology, a focusing target disposed on the compression sheet so it is visible when the compression sheet is closed directly over the specimen.

7. The method of claim 1 which further comprises enscribing a patient's name on a writing surface that accompanies the specimen during the diagnostic study.

8. The method of claim 1 in which removably attaching a specimen board and compression sheet is accomplished using a hook and loop fastener.

* * * * *